(12) United States Patent
Wilhelm et al.

(10) Patent No.: US 6,610,039 B1
(45) Date of Patent: Aug. 26, 2003

(54) ABSORBENT ARTICLE

(75) Inventors: Hoa La Wilhelm, Appleton, WI (US); Alan Francis Schleinz, Appleton, WI (US); David Louis Zenker, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 185 days.

(21) Appl. No.: 09/684,100

(22) Filed: Oct. 6, 2000

(51) Int. Cl.$^7$ .................................................. A61F 13/15
(52) U.S. Cl. ............................ 604/385.27; 604/385.01; 604/378; 604/365; 428/152; 428/125; 428/123
(58) Field of Search ........................... 604/585.27, 378, 604/385.01, 365; 428/152, 125, 123

(56) References Cited

U.S. PATENT DOCUMENTS

| | | |
|---|---|---|
| 3,901,236 A | 8/1975 | Assarsson et al. |
| 4,076,663 A | 2/1978 | Masuda et al. |
| 4,286,082 A | 8/1981 | Tsubakimoto et al. |
| 4,525,407 A * | 6/1985 | Ness ........................... 156/229 |
| 4,606,964 A * | 8/1986 | Wideman ................. 15/229.11 |
| 4,663,220 A | 5/1987 | Wisneski et al. |
| 4,699,823 A | 10/1987 | Kellenberger et al. |
| 4,704,116 A | 11/1987 | Enloe |
| 4,753,646 A | 6/1988 | Enloe |
| 4,891,258 A * | 1/1990 | Fahrenkrug ................. 428/131 |
| 4,895,568 A * | 1/1990 | Enloe .................... 604/385.27 |
| 4,916,005 A | 4/1990 | Lippert et al. |
| 4,938,753 A | 7/1990 | Van Gompel et al. |
| 5,019,073 A | 5/1991 | Roessler et al. |
| 5,226,992 A | 7/1993 | Morman |
| 5,399,219 A | 3/1995 | Roessler et al. |
| 5,486,166 A | 1/1996 | Bishop et al. |
| 5,490,846 A | 2/1996 | Ellis et al. |
| 5,527,300 A | 6/1996 | Sauer |
| 5,540,796 A | 7/1996 | Fries |
| 5,562,650 A | 10/1996 | Everett et al. |
| 5,593,400 A * | 1/1997 | O'Leary ................. 604/385.27 |
| 5,605,735 A | 2/1997 | Zehner et al. |
| 5,624,429 A | 4/1997 | Long et al. |

(List continued on next page.)

FOREIGN PATENT DOCUMENTS

| | | |
|---|---|---|
| EP | 0 217 032 A2 | 4/1987 |
| WO | WO 95/16425 | 6/1995 |

OTHER PUBLICATIONS

TAPPI Official Test Method T 543 om–94, "Bending Resistance of Paper (Gurley Type Tester)," published by the TAPPI Press, Atlanta, Georgia, pp. 1–7.
Federal Test Method Standard (FTMS) No. 191A, Method 5514, "Water Resistance of Cloth; Low Range, Hydrostatic Pressure Method," Jul. 20, 1978, 3 pages.

Primary Examiner—John J. Calvert
Assistant Examiner—Angela J Grayson
(74) Attorney, Agent, or Firm—Paul Yee; Thomas M. Parker

(57) ABSTRACT

An absorbent article (10) has a longitudinal direction (26) and a lateral direction (24). The article includes a backsheet layer (30), a liquid-permeable topsheet layer (28), and an absorbent body (32) sandwiched between the backsheet layer (30) and topsheet layer (28). A surge management member (46) is joined between the topsheet layer (28) and the absorbent body (32), and the surge management member (46) includes at least a first nonwoven fabric layer (52). In particular aspects, the article (10) can be bent around a wearer's body contours with a reduced tendency to form a transverse channel crease (76) along the cross-direction of the surge management member, particularly when the surge member (46) is curved through the wearer's crotch region. In further aspects, the article (10) can be bent around a predetermined radius of curvature substantially without forming, within the surge management member (46), a severe channel crease (76) that extends over a significant portion of a corresponding lateral width (78) of the surge management member (46).

25 Claims, 7 Drawing Sheets

U.S. PATENT DOCUMENTS

| | | | |
|---|---|---|---|
| 5,681,302 A | * 10/1997 | Melbye et al. | 604/373 |
| 5,683,374 A | * 11/1997 | Yamamoto et al. | 604/378 |
| 5,759,317 A | 6/1998 | Justmann | |
| 5,827,259 A | 10/1998 | Laux et al. | |
| 5,858,515 A | 1/1999 | Stokes et al. | |
| 5,904,675 A | 5/1999 | Laux et al. | |
| 5,993,433 A | * 11/1999 | St. Louis et al. | 604/385.27 |
| 6,030,373 A | 2/2000 | VanGompel et al. | |

* cited by examiner fold axis parallel to CD
MP-4 Copy Stand, Magnification = 1.3X fold axis parallel to CD
WILD M-420 Microscope, Magnification = 3.8X fold axis parallel to MD
MP-4 Copy Stand, Magnification = 1.3X fold axis parallel to MD
WILD M-420 Microscope, Magnification = 3.8X fold axis parallel to CD
MP-4 Copy Stand, Magnification = 1.3X fold axis parallel to CD
WILD M-420 Microscope, Magnification = 3.8X

ABSORBENT ARTICLE

FIELD OF THE INVENTION

The present invention relates to absorbent systems for garments and other articles. More particularly, the present invention relates to distinctive absorbent systems which can be employed with disposable articles, such as gowns, diapers, incontinence garments and the like.

BACKGROUND OF THE INVENTION

Conventional disposable absorbent articles have typically employed absorbent pads or other absorbent structures sandwiched between a backsheet layer and a liquid permeable liner layer. The absorbent structures have incorporated superabsorbent materials combined with fibrous matrices composed of natural and synthetic fibers. Typically, the absorbents structures have included superabsorbent particles mixed with cellulosic, woodpulp fluff. The absorbent articles have also included a surge management component which is configured to rapidly intake gushes of liquid, temporarily hold and distribute the liquid, and release the liquid to a storage component of the absorbent structure. Various arrangements of such surge management components have incorporated increased basis weights to provide desired levels of performance.

Conventional absorbent systems, such as those described above, have been excessively susceptible to leakage past the side edges of the absorbent, especially when the absorbent has been configured with a relatively narrow crotch region. In conventional arrangements, such as those described above, the article have tended to produce large, cross-directional creases or fold-lines during the placement of the article on a wearer, when the crotch region of the article is drawn up between the legs of the wearer and the article is curved into a generally U-shape. Such fold-lines have extended across the transverse widths of the surge management and liner components, and have undesirably acted as a troughs which liquids have followed to readily move toward and past the leg openings of the article. As a result, the conventional articles have remained susceptible to premature leakage, and there has been a continued need for absorbent systems that provide desired combinations of fit, comfort, and leakage resistance.

BRIEF DESCRIPTION OF THE INVENTION

Generally stated, the present invention provides a distinctive absorbent article having a longitudinal direction and a lateral direction. The article includes a backsheet layer, a liquid-permeable topsheet layer, and an absorbent body sandwiched between the backsheet layer and topsheet layer. A surge management member is joined between the topsheet layer and the absorbent body, and the surge management member can include at least a first nonwoven fibrous layer. In desired aspects, the article can be bent around a wearer's body contours with a reduced tendency to form a severe transverse channel crease along the cross-direction of the surge management member, particularly when the article is curved through the wearer's crotch region. In particular aspects, the article can be bent around a selected radius of curvature substantially without forming, within the surge management member, a gross channel crease that extends across a significant portion of a corresponding lateral width of the surge management member.

In other aspects, the surge management member can include a plurality of elastomeric filaments which are attached to at least the first fabric layer. In further aspects, an array of the elastomeric filaments can be attached to longitudinally compress at least the first fabric layer and to loft a thickness of the first fabric layer. In desired configurations, the plurality of elastomeric filaments are sandwiched between the first fabric layer and at least a second fabric layer, and the array of the elastomeric filaments can be attached to longitudinally compress the first and second fabric layers to loft an overall thickness of the first and second fabric layers.

The incorporation of the various aspects of the absorbent system of the invention can provide improved fit and absorbency with greater resistance to premature leakage past the leg openings of the article. Compared to conventional structures, the absorbent system of the invention can help reduce the tendency of urine or other liquids to run off a body side surface of the surge management and liner components along the transverse, cross-direction, and can thereby improve the leakage resistance of the article. The distinctively configured absorbent system of the invention can advantageously provide improved properties, such as improved combinations of attractive appearance, good fit, increased comfort to the wearer and reduced leakage.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The various aspects and embodiments of the invention will be described in the context of a disposable absorbent article, such as a disposable diaper. It is, however, readily apparent that the present invention could also be employed with other articles, such as caps, gowns, shoe covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer.

Figure 1:
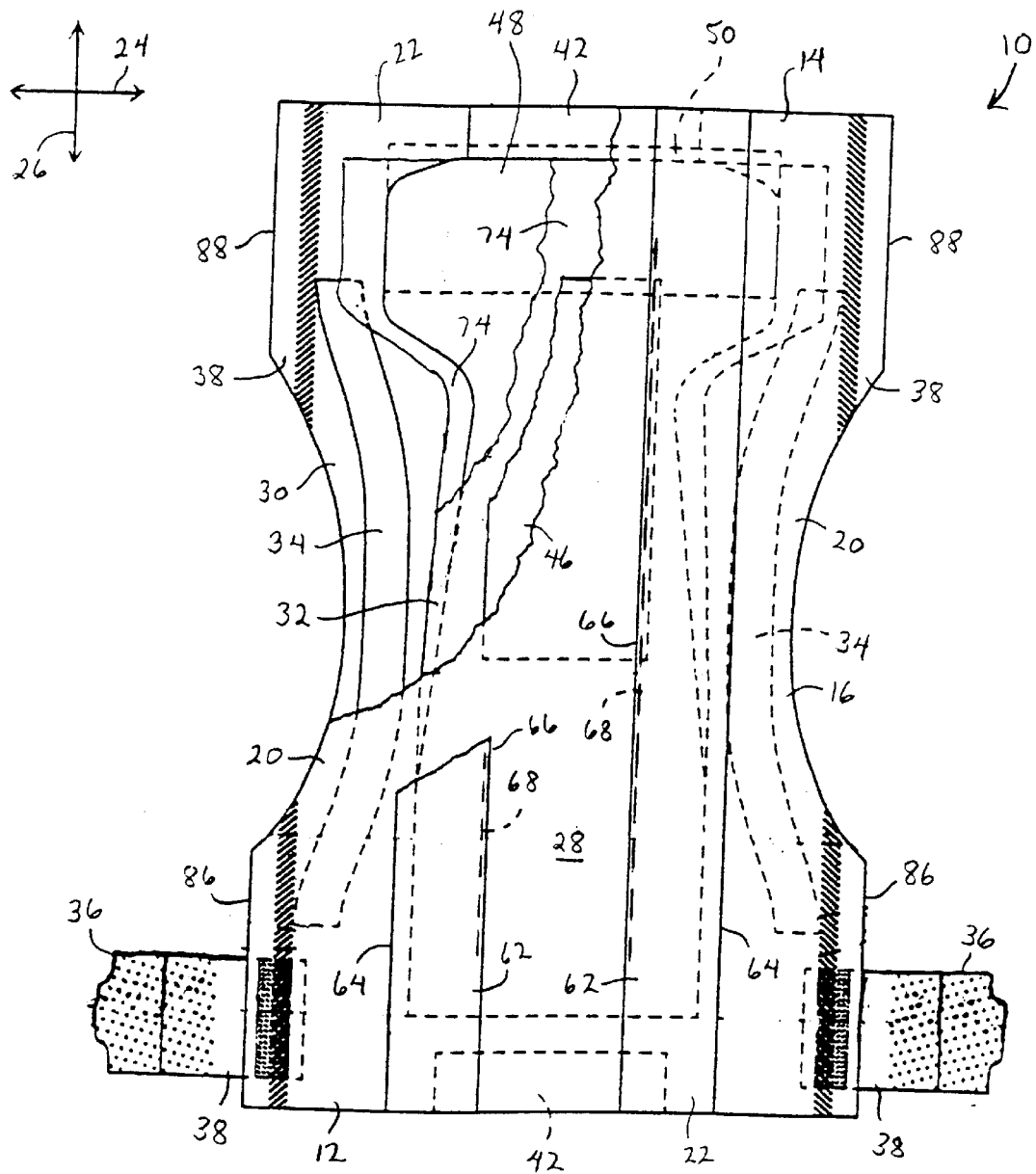
FIG. 1 representatively shows a partially cut-away, top plan view of an inward side of a diaper article which incorporates the absorbent system of the invention.
Figure 2:
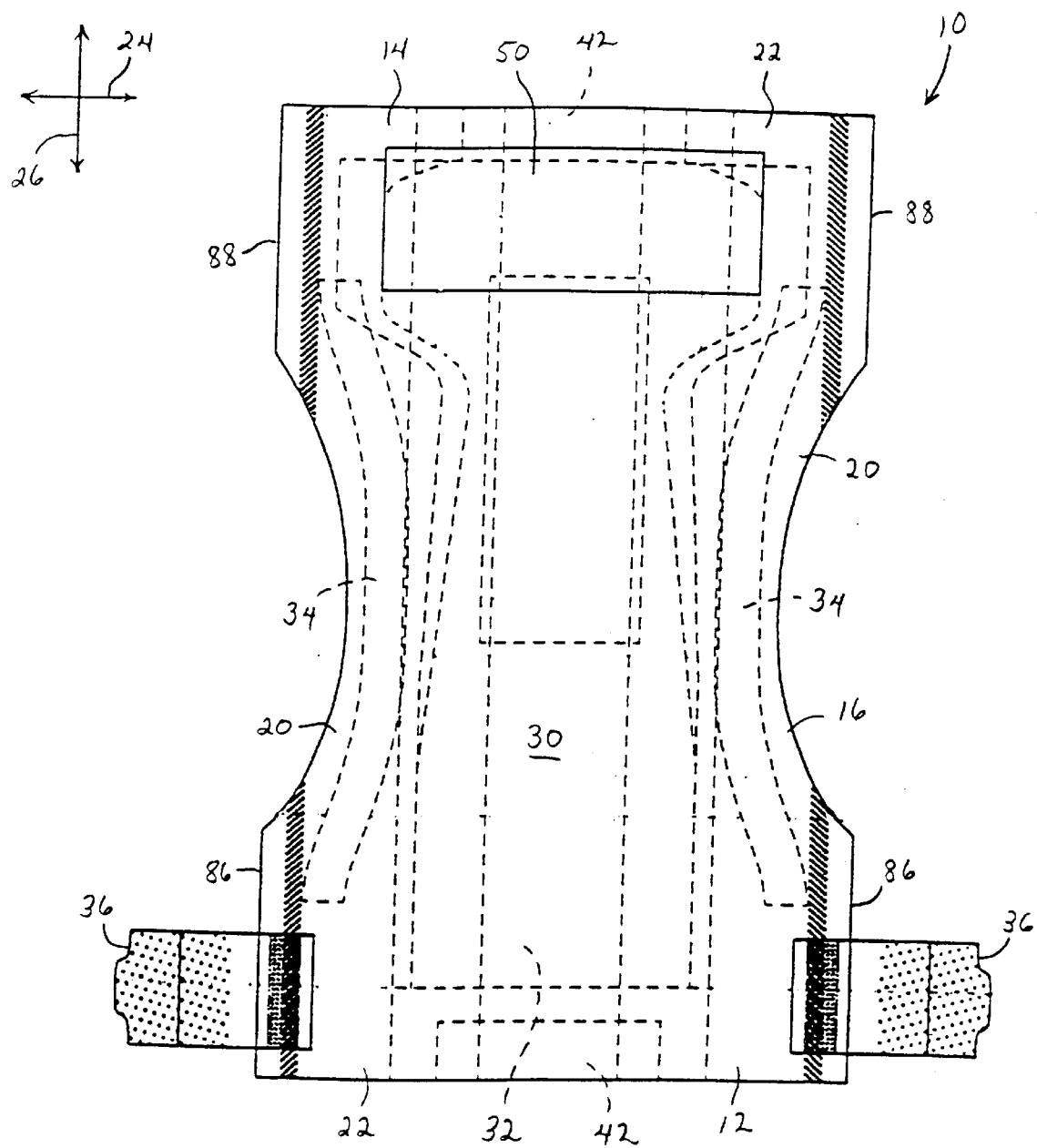
FIG. 2 representatively shows a top, plan view of an outward side of a diaper article which incorporates the absorbent system of the invention.
Figure 4:
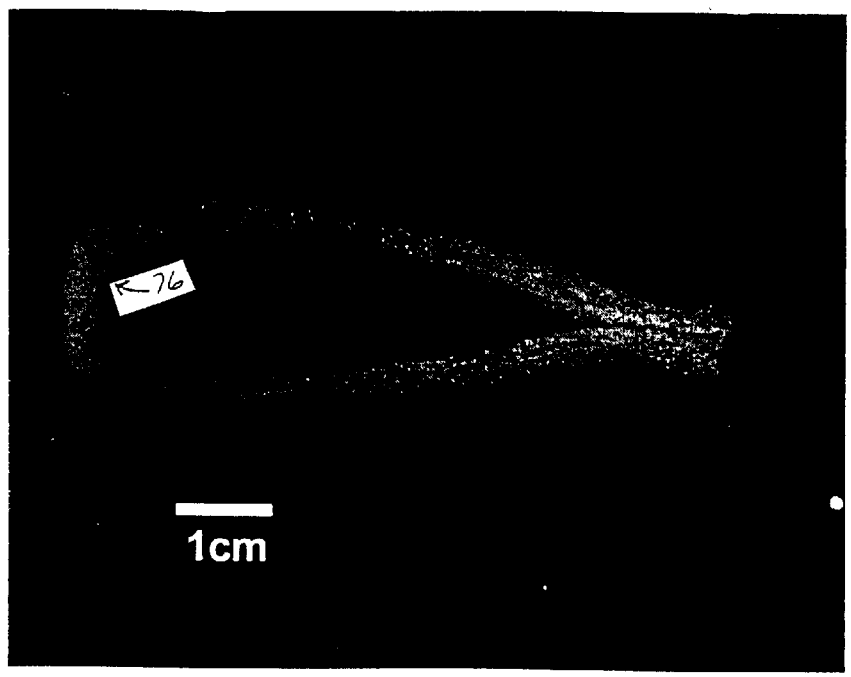
FIG. 4 representatively shows an edge-wise, side view of a curved surge management member in which excessively large creases or folds have formed.
Figure 4A:
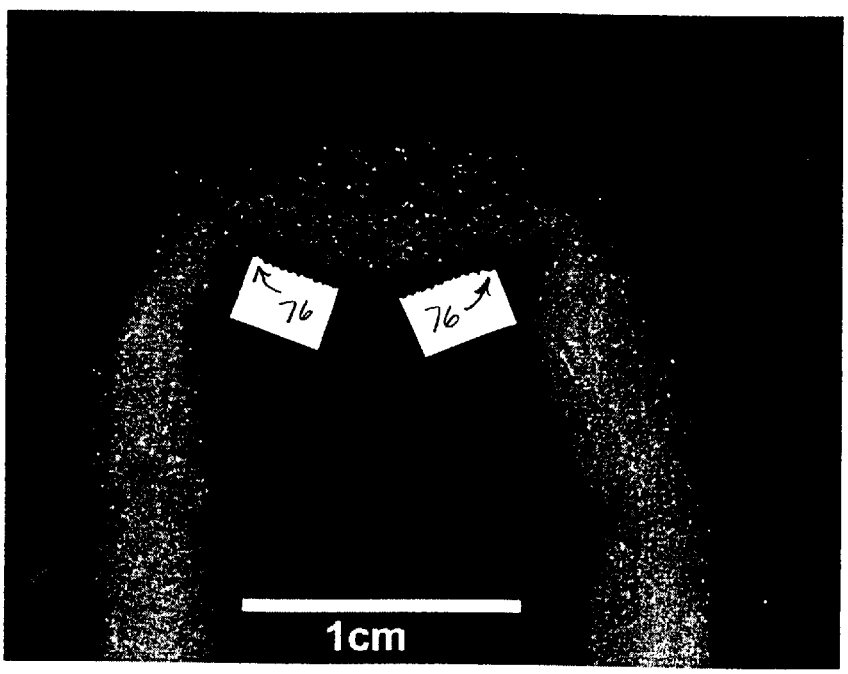
FIG. 4A representatively shows an enlarged edge-wise, side view of the curved surge management member illustrated in FIG. 4.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. With reference to FIGS. 1 and 2, an article, such as the representatively shown diaper article 10, has a longitudinal direction 26 and a lateral direction 24. The article includes a backsheet layer 30, a liquid-permeable topsheet layer 28, and an absorbent body 32 sandwiched between the backsheet layer 30 and topsheet layer 28. A surge management member 46 is joined between the topsheet layer 28 and the absorbent body 32, and the surge management member 46 desirably includes at least a first nonwoven fibrous layer, such as provided by the shown nonwoven fabric layer 52. The article 10 can be bent around a wearer's body contours with a reduced tendency of forming an excessively large transverse channel crease 76 (e.g. FIGS. 4 and 4A) along the cross-direction of the surge management member, particularly when the surge member 46 is curved through the wearer's crotch region. Desirably, the article and surge management member can be bent around a wearer's body contours substantially without forming a significant transverse channel crease.

In particular aspects, the article 10 (and particularly the surge management member 46) can be bent around a selected radius of curvature, such as radius of 1 cm, substantially without forming, within the surge management member 46, a severe channel crease 76 that extends across a significant portion or percentage of a width of the surge management member 46 at the portion of the surge member that corresponds to the location of the channel crease. Other aspects of the invention can include a surge management member 46 having a plurality of elastomeric filaments 54 which are attached to at least the first fabric layer 52. In desired aspects, the elastomeric filaments are arranged to extend substantially along the longitudinal direction 26 of the surge management member. In further aspects, an array of the elastomeric filaments 54 can be attached to longitudinally compress at least the first fabric layer 52 and to loft a thickness 58 of the first fabric layer (e.g. FIG. 5A). Still other aspects of the invention can include the first fabric layer 52 and at least a second fabric layer 56. Additionally, the elastomeric filaments 54 can be sandwiched between the first and second fabric layers, and can be configured to longitudinally compress and loft the overall thickness 58a (e.g. FIG. 5B) of the first and second fabric layers 52 and 56 of the surge management member 46. Desirably, the fabric layers are composed of nonwoven fabrics, but may include woven or knitted fabrics, if desired.

In prior, conventional articles with surge management portions or members, the surge member has been relatively stiff and non-elastic even when configured with a low density. When a web of surge material is bowed into a curved shape, the outside-facing, convex surface of the material is under tension while the inside-facing, concave surface is under compression. As a result, one or more cross-direction creases or folds can form on the inside-facing surface of the surge member, and can extend generally parallel to the bending axis about which the bending moment is applied. Thus, the surge member has tended to produce deep transverse-direction fold lines in the article when the diaper is applied to the wearer and is subsequently curved into a U-shape. This problem has been aggravated where an increased-density "skin layer" has been present on the major facing surfaces of the fibrous web material employed for the surge member.

In ordinary constructions, the surge layer is typically attached (e.g. adhesively attached) to the body side liner or topsheet layer 28. Accordingly, the buckling or folding of surge layer can also produce buckling and folding in the topsheet layer. Each transverse fold in the topsheet and surge member can act as a trough or channel which liquids can readily follow. The channels can provide relatively unobstructed pathways toward the leg opening, and can cause premature leakage. The presence of the channels is especially undesirable when the absorbent core structure has a narrow crotch width, because the narrow crotch width has less absorbent material to collect any incidental liquid that may "runoff" over or past the terminal sided edges of the surge member 46.

In the various aspects and configurations of the surge member employed in the present invention, the fibrous material in the compressed portion of the surge member can advantageously "pack" closer together without producing deleterious troughs or channel creases, and without producing in the compressed portion of the surge member an overly high density that can excessively degrade the rate of liquid intake. The distinctive aspects of the present invention (individually and in combination) can advantageously help to reduce leakage from the absorbent article. The article of the invention can advantageously reduce the formation of large, transversely extending, creases or fold-lines, particularly in the surge management and topsheet components of the article. Such undesired creases or folds can be excessively large and deep and can cause premature leakage. By incorporating the various aspects of the surge management component 46, the article of the invention can advantageously reduce the occurrence of gross wrinkles and channel creases that extend along the lateral, cross-direction of the surge management member when the article is curved around the contours of a wearer's body during ordinary use. Additionally, the article can exhibit fewer gross wrinkles and channel creases that extend along the lateral, cross-direction of the topsheet layer 28. The article can exhibit an improved penetration and movement of liquid through the topsheet 28 and the surge management member 46, and into the absorbent body structure 32. The liquid appointed for absorption can also be better distributed along the longitudinal direction 26 of the article, and less liquid can be channeled past the side edges of the absorbent body structure. Accordingly, the article of the invention can exhibit reduced leakage past the side edges of the article. As a result, the various aspects and configurations of the invention can help provide desired combinations of attractive appearance, good fit, improved comfort and improved resistance to premature leakage.

The article of the invention can, for example, be a garment provided by the representatively shown disposable diaper 10. In desired configurations, the first article portion can provide a first waistband portion, such as the shown back waistband portion 12, and the second article portion can provide a second waistband portion, such as the shown front waistband portion 14. The article can additionally have an intermediate or crotch portion 16 which interconnects between the first and second waistband portions 12 and 14, respectively. The article can further include a backsheet layer 30, a liquid permeable topsheet layer 28 connected and assembled in facing relation with the backsheet layer, and an absorbent structure, such as a structure which includes absorbent body 32. The absorbent structure is sandwiched between the backsheet and topsheet layers, and is operably held therebetween. An operative fastening system, such as the shown system having fasteners 36, is typically constructed and arranged to interconnect the first waistband portion 12 with the second waistband portion 14 to hold the article on a wearer. The fastening system can be operatively configured to join the first, back waistband portion 12 in an overlapping relation with the second, front waistband portion 14 in a back-to-front arrangement to thereby encircle the wearer's body and hold the diaper secure on the wearer during use. Optionally, the fastening system can employ fasteners 36 which are configured to join the front waistband portion 14 in an overlapping relation with the back waistband portion 12 in a front-to-back arrangement to secure the diaper. In such optional arrangements, the front waistband region may be identified as the first waistband portion 12 and the rear waistband region may be identified as the second waistband portion 14.

The front waistband section 14 of the representatively shown diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article can also have an appointed fastener landing zone member 50 which is disposed on the outward surface of the article. In the configuration shown in FIGS. 1 and 2, for example, the landing member 50 is disposed on the outward surface of the backsheet layer 30. The liquid permeable topsheet layer 28 is superposed in facing relation with the backsheet layer 30, and the absorbent body 32 is operably connected and affixed between the backsheet layer 30 and topsheet layer 28.

FIGS. 1 and 2 show typical plan views of the representative disposable diaper 10 in its generally flat-out, uncontracted state (i.e., with substantially all elastic induced gathering and contraction removed). In FIG. 1, portions of the structure are partially cut away to more clearly show the interior construction of the diaper article, and the bodyside surface of the diaper which contacts the wearer is facing the viewer. The outer edges of the diaper define a periphery with longitudinally extending side edge margins 20 and laterally extending end edge margins 22. The side edges define leg openings for the diaper, and optionally, are curvilinear and contoured. The end edges are shown as straight, but optionally, may be curvilinear.

With regard to the designated surfaces of the article, the various inward or bodyside surfaces are configured to face toward the body of the wearer when the article is placed about the wearer. The designated outward surfaces of the article are configured to face away from the wearer's body when the article is placed about the wearer.

Figure 3:
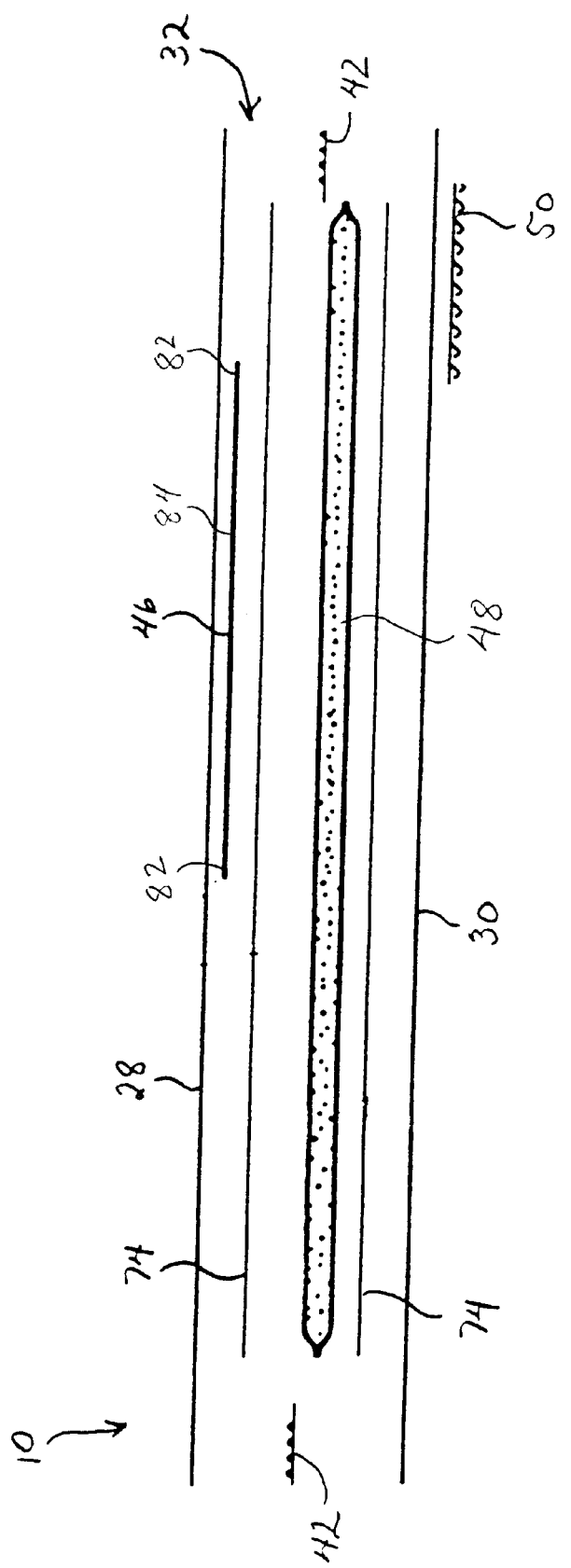
FIG. 3 representatively shows a schematic, longitudinal cross-sectional view of the article illustrated in FIG. 1.

With reference to FIGS. 1, 2 and 3, the diaper 10 can typically include the porous, liquid permeable topsheet 28; the substantially liquid impermeable backsheet 30; the absorbent body structure 32 positioned and connected between the topsheet and backsheet; the surge management portion or member 46 located adjacent the absorbent structure; and a system of elastomeric gathering or gasketing members, such as a system including leg elastics 34 and waist elastics 42. The surge management portion is positioned in a liquid communication with an appointed storage or retention portion 48 of the absorbent structure. Additionally, the various components, such as the topsheet 28, backsheet 30, absorbent structure 32, surge management portion 46 and elastic members 34 and 42, may be assembled together into a variety of well-known diaper configurations. The diaper can additionally include a system of containment flaps 62, and a system of side panel or ear region members 38, which may be elasticized or otherwise rendered elastomeric, as desired.

Examples of articles which include elasticized side panels and selectively configured fastener tabs are described in U.S. patent application Ser. No. 168,615 of T. Roessler et al., entitled DYNAMIC FITTING DIAPER, and filed Dec. 6, 1993; which corresponds to WO95/16425 published Jun. 22, 1995. Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER which issued Mar. 21, 1995; in U.S. Pat. No. 5,540,796 entitled A PROCESS FOR ASSEMBLING ELASTICIZED EAR PORTIONS by D. Fries, which issued Jul. 30, 1996; and in U.S. Pat. No. 5,759,317 entitled PROCESS FOR MAKING A MECHANICAL FASTENER by D. A. Justmann, which issued Jun. 2, 1998. The disclosures of the above-described documents are incorporated herein by reference in a manner that is consistent (not in conflict) herewith.

The diaper 10 generally defines the longitudinally extending length direction 26 and the laterally extending width direction 24, as representatively shown in FIGS. 1 and 2. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and may have length and width dimensions which are generally larger than and extend beyond the corresponding dimensions of the absorbent structure 32 to provide for the corresponding side margins 20 and end margins 22. Optionally, the topsheet and backsheet layers may not be coextensive. The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. The intermediate, crotch region 16 lies between and interconnects the waistband regions 14 and 12, and comprises that portion of the diaper which, when worn, is positioned between the legs of the wearer and covers the lower torso of the wearer. Thus, the intermediate crotch region 16 is an area where repeated fluid surges typically occur in the diaper or other disposable absorbent article.

The backsheet 30 can typically be located along an outer-side surface of the absorbent body 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present disclosure, the term "flexible" refers to materials which are compliant and which will readily conform to the general shape and contours of the wearer's body. Backsheet 30 prevents the exudates contained in absorbent body 32 from wetting articles, such as bedsheets and overgarments, which contact diaper 10. In particular embodiments of the invention, backsheet 30 can include a film, such as a polyethylene film, having a thickness of from about 0.013 millimeters (0.5 mil) to about 0.051 millimeters (2.0 mils). For example, the backsheet film can have a thickness of about 0.032 millimeters (1.25 mil).

Alternative constructions of the backsheet may comprise a woven or non-woven fibrous web layer which has been totally or partially constructed or treated to impart the desired levels of liquid impermeability to selected regions that are adjacent or proximate the absorbent body. For example, the backsheet may include a gas-permeable, non-woven fabric layer laminated to an appointed facing surface of a polymer film layer which may or may not be gas-permeable. Ordinarily, the fabric layer is attached to an outward-facing surface of the polymer film layer. Other examples of fibrous, cloth-like backsheet materials can comprise a stretch-thinned or a stretch-thermal-laminate material composed of a 0.6 mil (0.015 mm) thick polypropylene blown film and a 0.7 ounce per square yard (23.8 gsm) polypropylene spunbond material (2 denier fibers).

In particular arrangements, a substantially liquid impermeable, vapor permeable backsheet layer may be a composite material which includes a vapor permeable film layer adhesively laminated to a spunbond layer. The vapor permeable film layer can be obtained from the Tredegar Film Products division of Tredegar Industries, Inc., under the tradename EXAIRE. The film layer can include 48–60 weight percent (wt %) linear low-density polyethylene and 38–50 wt % calcium carbonate particulates which may be uniformly dispersed and extruded into the film layer. The film layer can be stretched to have a thickness of about 0.7 mil (about 0.018 mm) and a basis weight of 16–22 grams per square meter ($g/m^2$). The spunbond layer can be adhesively laminated to the film layer, and can have a basis weight of about 27 $g/m^2$. The spunbond layer can be made using conventional spunbond technology, and can include filaments of polypropylene having a fiber denier of 1.5–3 dpf. The vapor-permeable film layer may be adhered to the spunbond layer using a pressure sensitive, hot melt adhesive at an add-on rate of about 1.6 $g/m^2$, and the adhesive can be deposited in the form of a pattern of adhesive swirls or a random fine fiber spray.

The liquid impermeable, vapor permeable backsheet layer may alternatively include a highly breathable stretch thermal laminate material (HBSTL). The HBSTL material can include a polypropylene spunbond material thermally attached to a stretched breathable film. For example, the HBSTL material may include a 0.6 osy (20.4 $g/m^2$) polypropylene spunbond material thermally attached to an 18.7 $g/m^2$ stretched breathable film. The breathable film may include two skin layers with each skin layer composed of 1–3 wt % EVA/catalloy. The breathable film may also include 55–60 wt % calcium carbonate particulates, linear low-density polyethylene, and up to 4.8% low density polyethylene. The stretched breathable film can include a thickness of 0.45–0.50 mils (0.011–0.013 mm) and a basis weight of 18.7 $g/m^2$. The spunbond layer can be thermally bonded to the breathable film, and can have a basis weight of about 20.4 $g/m^2$. The spunbond layer can have a fiber denier of 1.5–3 dpf, and the stretched breathable film can be thermally attached to the spunbond material using a "C-star" pattern which provides an overall bond area of 15–20%.

The various types of such materials have been employed to form the backsheet or outercover of HUGGIES disposable diapers, which are commercially available from Kimberly-Clark Corporation. The backsheet 30 typically provides the outermost cover layer of the article. Optionally, however, the article may include a separate outer cover component member which is additional to the backsheet. The backsheet may also be embossed or otherwise provided with a pattern or matte finish to exhibit a more aesthetically pleasing appearance.

As mentioned, the backsheet 30 may include a microporous, "breathable" material which permits gases, such as water vapor, to escape from the absorbent body 32 while substantially preventing liquid exudates from passing through the backsheet. For example, the breathable backsheet may be composed of a microporous polymer film or a nonwoven fabric which has been coated or otherwise modified to impart a desired level of liquid impermeability. Another example of a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn.

In the various configurations of the invention, where a component such as the backsheet 30 or the containment flaps 62 are configured to be permeable to gas while having a resistance and limited permeability to aqueous liquid, the liquid resistant material can have a construction which is capable of supporting a selected hydrohead of water substantially without leakage therethrough. For example, desired materials can support a hydrohead of at least about 45 cm of water substantially without leakage therethrough. A suitable technique for determining the resistance of a material to liquid penetration is Federal Test Method Standard FTMS 191 Method 5514, 1978, or an equivalent thereof.

The size of the backsheet 30 is typically determined by the size of absorbent body 32 and the particular diaper design selected. Backsheet 30, for example, may have a generally T-shape, a generally I-shape or a modified hourglass shape, and may extend beyond the terminal edges of absorbent body 32 by a selected distance, such as a distance within the range of about 1.3 centimeters to 2.5 centimeters (about 0.5 to 1 inch), to provide at least a portion of the side and end margins.

The topsheet 28 presents a body-facing surface which is compliant, soft feeling, and non-irritating to the wearer's skin. Further, the topsheet 28 can be less hydrophilic than absorbent body 32, and is sufficiently porous to be liquid permeable, permitting liquid to readily penetrate through its thickness to reach the absorbent body. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent body 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present disclosure, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% TRITON X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by suitable attachment mechanisms (not shown) such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the topsheet 28 to the backsheet 30. It should be readily appreciated that the above-described attachment mechanisms may also be employed to suitably interconnect, assemble and/or affix together the various other component parts of the articles which are described herein.

The absorbent body 32 provides an absorbent structure which can include the retention portion 48, such as the representatively shown absorbent pad composed of selected hydrophilic fibers and high-absorbency particles, for holding and storing absorbed liquids and other waste materials. The absorbent body is positioned and sandwiched between the topsheet 28 and backsheet 30 to form the diaper 10. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure 32 can comprise a matrix of hydrophilic fibers, such as a web of cellulosic fluff, mixed with particles of high-absorbency material. In particular arrangements, absorbent body 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in the absorbent body 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in the absorbent body 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–1200 gsm. In certain aspects of the invention, the average composite basis weight is within the range of about 500–1000 gsm, and alternatively is within the range of about 550–800 gsm to provide desired performance.

To improve the containment of the high-absorbency material, absorbent body structure 32 can include an overwrap, such as wrap sheet 74, which is placed immediately adjacent and around absorbent body 32 and may be bonded to the absorbent structure and to the various other components of the article. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 74, or at least the bodyside layer of the wrap sheet, may comprise a meltblown web composed of meltblown fibers, such as meltblown polypropylene fibers. Another example of absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of absorbent body 32. Such a configuration of the wrap sheet can, for example, facilitate the formation of a substantially complete sealing and closure around the peripheral edges of absorbent body 32. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 74 can extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Diaper 10 can also include a surge management layer 46 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. In the illustrated embodiment, for example, surge layer 46 can be located on an inwardly facing body side surface of topsheet layer 28. Alternatively, surge layer 46 may be located adjacent to an outer side surface of topsheet 28. Accordingly, the surge layer would then be interposed between topsheet 28 and absorbent body 32. Examples of suitable surge management layers 46 are described in U.S. Pat. No. 5,486,166 entitled FIBROUS NONWOVEN WEB SURGE LAYER FOR PERSONAL CARE ABSORBENT ARTICLES AND THE LIKE by C. Ellis and D. Bishop, which issued Jan. 23, 1996; and U.S. Pat. No. 5,490,846 entitled IMPROVED SURGE MANAGEMENT FIBROUS NONWOVEN WEB FOR PER- SONAL CARE ABSORBENT ARTICLES AND THE LIKE by C. Ellis and R. Everett, which issued Feb. 13, 1996; the entire disclosures of which are hereby incorporated by reference in a manner that is consistent herewith.

With reference again to FIGS. 1 and 3, the representatively shown surge management member 46 is joined between the topsheet layer 28 and the absorbent body 32, and the surge management member 46 has a pair of longitudinally opposed, terminal end regions 82, and an intermediate region 84, which is located between the end regions 82. The surge management member 46 has a pair of longitudinally opposed, terminal end regions 82. In desired configurations, the intermediate region 84 and at least one of the end regions 82 can be attached to the topsheet layer 28. Accordingly, either or both of the end regions 82 can be attached to the topsheet layer. Desired configurations of the surge management member 46 can include at least a first nonwoven fibrous layer, such as provided by the shown nonwoven fabric layer 52. The article 10 can advantageously be bent around a wearer's body contours without forming a deleterious, transverse channel crease 76 (e.g. FIGS. 4 and 4A) along a significantly extensive portion of the cross-direction of the surge management member, particularly when the dry surge member 46 is bent and curved through the wearer's crotch region during the wearing of the article.

In particular aspects, the article 10 can be bent around a radius of curvature of 1 cm substantially without forming, within the surge management member 46 a deep, severe channel crease 76 that extends more than about 50% of a corresponding lateral width 44 (e.g. FIG. 5) of the surge management member 46 at the location of the channel crease.

In particular aspects, the surge management member 46 can include at least one web composed of a longitudinally compressible material, such as a longitudinally compressible nonwoven fabric. Examples of such longitudinally compressible nonwoven materials can include a fibrous web which has a struto-like configuration that orients the fibrous filaments more vertically within the web; needle-punched web; a web with filament roving; a web composed of filament tow; a web composed of foam; and the like, as well as combinations thereof. The longitudinally compressible-web of nonwoven material can have a web density which is at least a minimum of about 0.001 g/cm$^3$. The web density can alternatively be at least about 0.005 g/cm$^3$, and optionally, can be at least about 0.01 g/cm$^3$ to provide improved performance. In other aspects, the web density can be not more than a maximum of about 0.03 g/cm$^3$. The web density can alternatively be not more than about 0.025 g/cm$^3$, and optionally, can be not more than about 0.02 g/cm$^3$ to provide improved effectiveness. Where the surge management member has been subjected to compression or lofting operations, such as by the contraction of component elastomeric strands attached and assembled into the surge member, the density of overall thickness of the surge management member is determined after the compression or lofting operations, e. g. after the elastomeric strands have been allowed to contract.

If the web density of the material of the surge management member is too low, the surge member may not adequately drain liquid from the topsheet 28, and may cause excessive dampness against the wearer's skin. The surge member also may not adequately decelerate and diffuse the surges or gushes of liquid that are introduced into the article. Additionally, the surge management layer may not adequately accept and temporarily hold the liquid prior to releasing the liquid into the storage or retention portions of the absorbent structure. If the web density is too large, the surge member can have insufficient void volume to provide the desired rapid intake of liquid, and the surge member can be excessively susceptible to the formation of gross creases that extend across the transverse width 44 of the surge member.

The surge management member can include various types of fabrics, such as spunbond fabrics, meltblown fabrics, bonded carded webs, through-air bonded carded webs, knit fabrics, woven fabrics, airformed fabrics and the like, as well as combinations thereof. The fabrics can be composed of various types of fibers, such as polyolefin fibers, polyester fibers, bicomponent fibers, conjugate fibers, and the like, as well as combinations thereof.

In optional configurations of the invention, the surge management member 46 can include a generally monolithic nonwoven fabric composed of elastomeric fibers. The elastomeric nonwoven fabric can, for example, be composed of various elastomeric staple fibers, elastomeric binder fibers or the like, as well as combinations thereof.

The surge management member can have "expansion joints" that are cut or otherwise formed into the member to allow an improved ability to bend around compound curves. The surge member may alternatively include pleats or hinge lines, and may optionally be creped or corrugated. Additionally, the surge member may or may not be extensible or retractable.

Desired configurations of the surge management member can include a composite laminate which can bend around the contours of a wearer's body, particularly the contours that extend through the wearer's crotch region, without producing excessive cross-directional, channel creases or folds.

Figure 5:
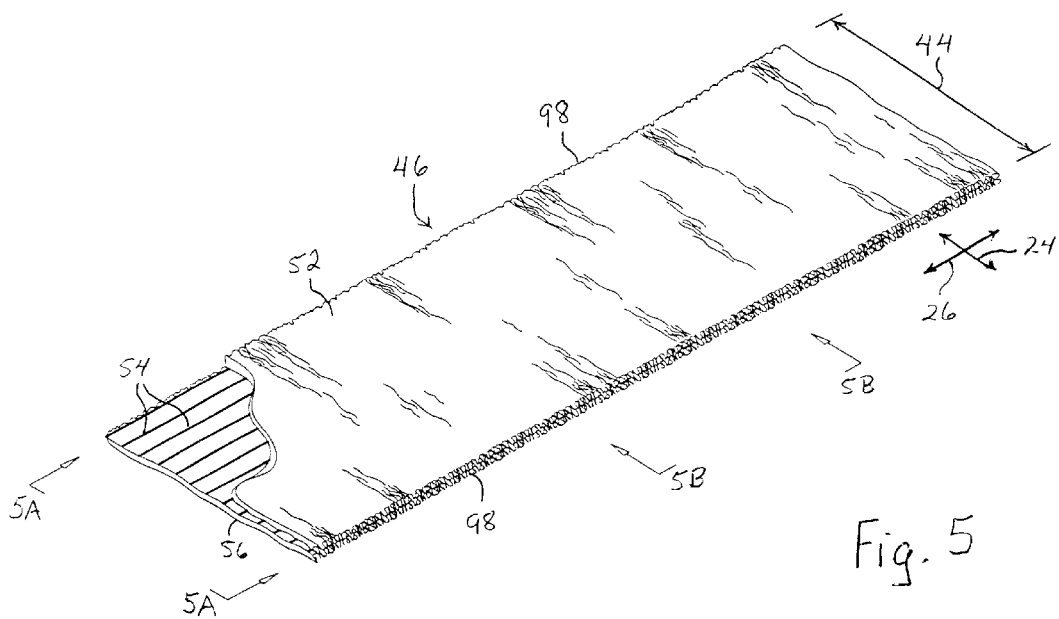
FIG. 5 representatively shows a schematic perspective view of a surge management member having a plurality of elastomeric filaments sandwiched and attached between first and second nonwoven fabric layers to operatively compress and loft the fabric layers.
Figure 5A:
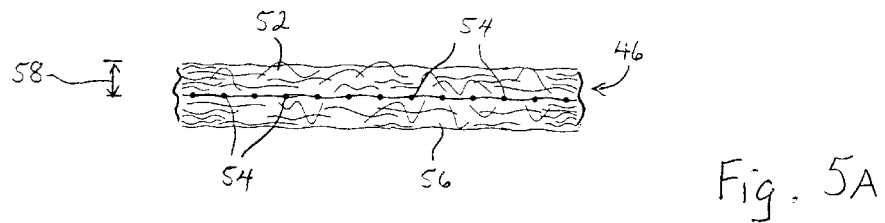
FIG. 5A representatively shows a schematic side edge view along region 5A—5A of the surge management member illustrated in FIG. 5.
Figure 5B:
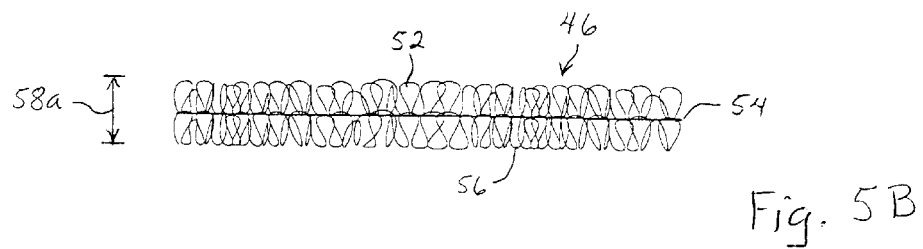
FIG. 5B representatively shows a schematic cross-sectional, end view along region 5B—5B of the surge management member shown in FIG. 5.
Figure 6:
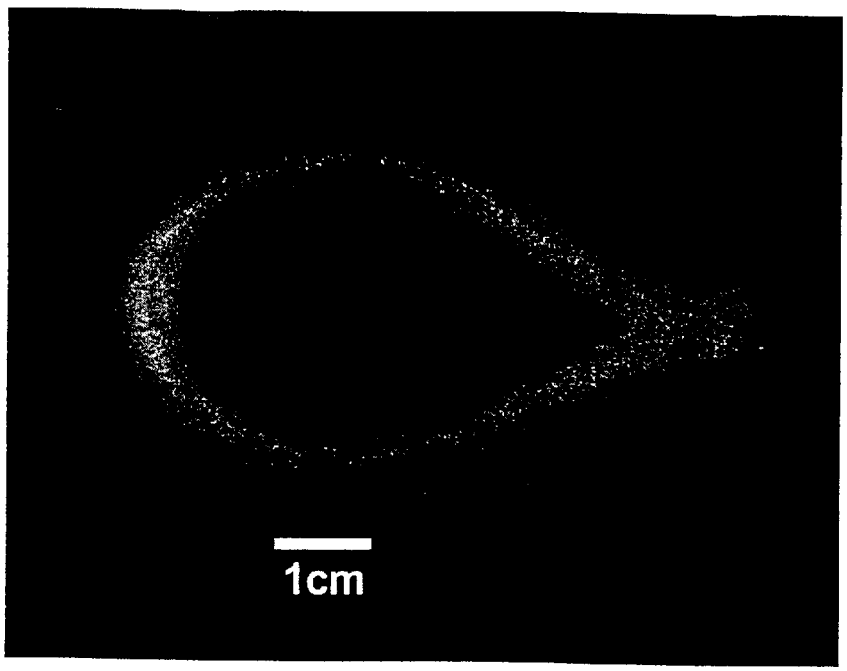
FIG. 6 representatively shows an edge-wise, side view of a surge management member of the invention which includes an array of elastomeric filaments sandwiched between a pair of nonwoven fibrous web layers, and substantially avoids the formation of excessively large creases or folds when curved about an axis that extends generally parallel to a cross-direction of the surge management member.
Figure 6A:
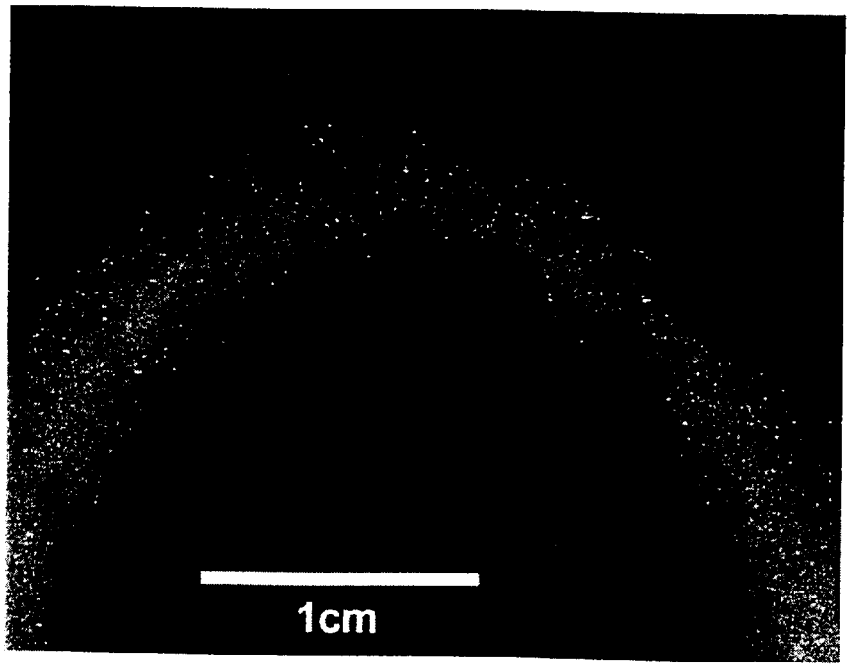
FIG. 6A representatively shows an enlarged edge-wise, side view of the curved surge management member illustrated in FIG. 6.
Figure 7:
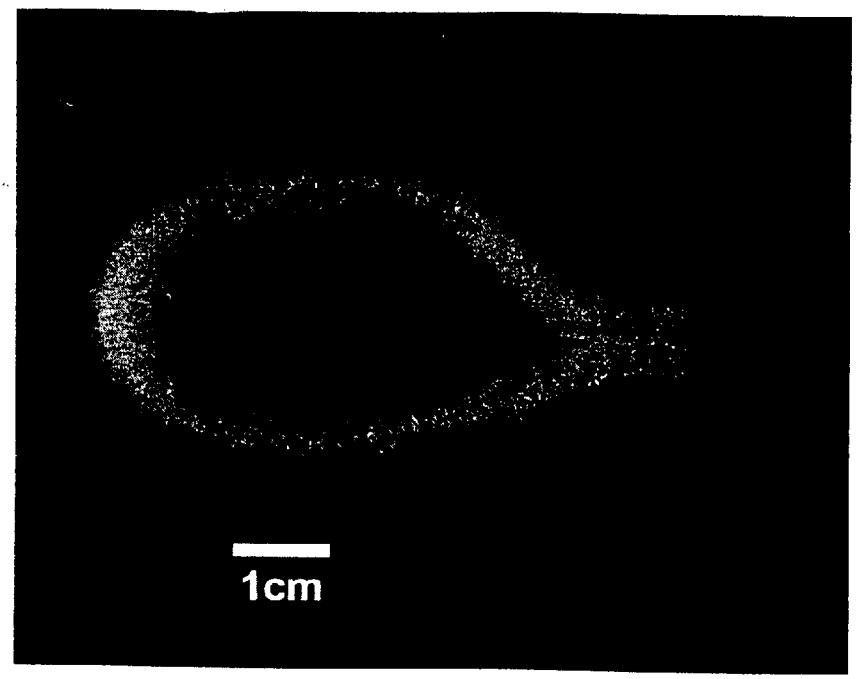
FIG. 7 representatively shows an edge-wise, side view of another surge management member of the invention which includes an array of elastomeric filaments sandwiched between a pair of nonwoven fibrous web layers, and substantially avoids the formation of excessive creases or folds when curved about an axis that extends generally parallel to a longitudinal-direction of the surge management member.
Figure 7A:
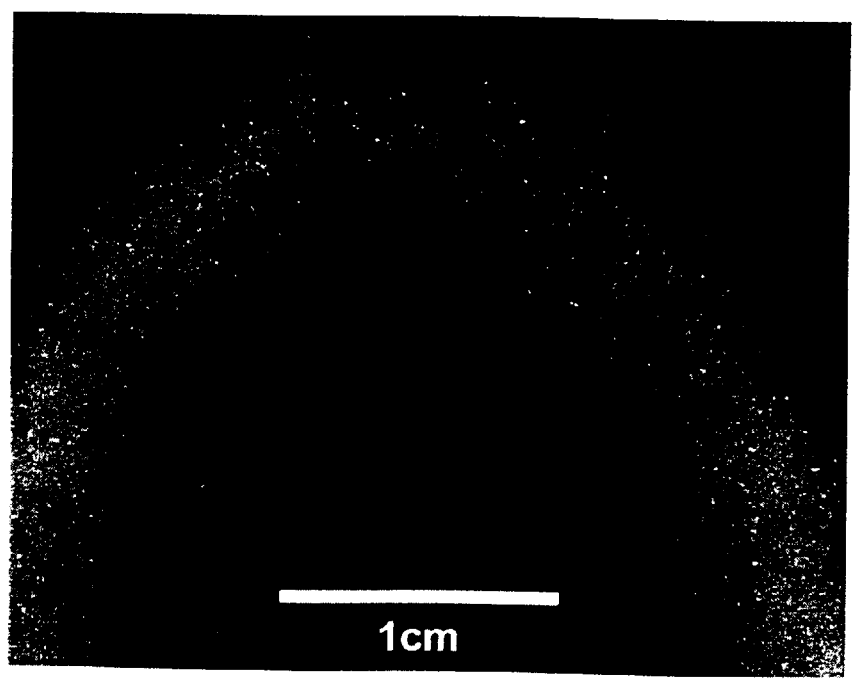
FIG. 7A representatively shows an enlarged edge-wise, side view of the curved surge management member illustrated in FIG. 7.

With reference to FIG. 1 and FIGS. 5 through 5B, the present invention can include a surge management member 46 having a plurality of elastomeric filaments 54 which are attached to at least the first fabric layer 52. In particular configurations, the elastomeric filaments are arranged to extend substantially along the longitudinal direction 26 of the surge management member. In desired configurations, an array of the elastomeric filaments 54 can be attached to longitudinally compress at least the first fabric layer 52 and to loft a thickness 58 of the first fabric layer.

Still other aspects of the invention can include at least a second fabric layer 56, and the elastomeric filaments 54 can be configured to longitudinally compress and loft the first and second nonwoven fabric layers 52 and 56 of the surge management member 46. For example, the surge member 46 can include two, very low basis weight layers or plies of fibrous material, and a plurality of elastomeric filaments can be sandwiched and held between the two plies.

Desirably, the selected fibrous plies and elastomer filaments are operatively assembled and joined by a very low add-on of adhesive, and the elastomer filaments have been tensioned and stretched prior to their joining between the fibrous plies. Upon a release of the tension applied to the elastomer filaments, the filaments can contract and compress the fibrous layers of the laminate, and can re-orient an operative portion of the fibers into an increased alignment along the z-directional thickness of the laminate. This can provide a multiplicity of micro-scale, lofty areas among the surge material fibers. The lofty regions are dispersed over the area of the surge member 46, and have a low density.

Additionally, the lofty regions are resiliently compressible and expandable, particularly along the direction of contraction generated by the retracting elastomer filaments. The low density and loftiness of the surge management member can allow an operative amount of fiber "packing" along a concave surface of the surge member that is formed when the surge member is bent around a wearer's body. Additionally, the resiliently compressed, concave surface of the surge member can still maintain open inter-fiber spacings that provide a sufficiently large pore sizes along concave surface of the surge member. The large pore sizes can provide an adequate intake rate of absorbed liquid even when the finished laminate is bent into a relatively small radius of curvature, such as a radius of 1 cm.

Another aspect of the invention can include a surge management member 46 which has a thickness dimension 58a and includes the first nonwoven fabric layer 52, and at least the second nonwoven fabric layer 56. A plurality of the elastomeric filaments 54 can be attached between the first and second nonwoven fabric layers, and in desired configurations, the elastomeric filaments 54 are attached to at least one of the first and second nonwoven fabric layers 52 and 56 of the surge management member 46 to longitudinally compress the first and second fabric layers, and to loft an overall total thickness of the first and second fabric layers. Accordingly, the elastomeric filaments 54 can operatively compress the first and second fabric layers, and loft the thickness 58a of the surge management member.

Various nonwoven fabric materials can be employed to construct the selected layers within the surge management member 46. Examples of such nonwoven fabric materials can include spunbonded webs, meltblown webs, bonded carded webs, airformed webs, airlaid webs, wet-laid webs, and foam webs, or the like, as well as combinations thereof. In desired configurations, one or more of the nonwoven fabric layers of the surge management member can include a spunbonded web composed of polyethylene and polypropylene bicomponent fibers.

Each of the nonwoven fabric layers employed in the surge management member 46 can be composed of fibers having a selected denier. In particular aspects, the fiber denier can be at least a minimum of about 0.9 d. The fiber denier can alternatively be at least about 2 d, and optionally, can be at least about 3 d to provide improved performance. In other aspects, the fiber denier can be not more than a maximum of about 18 d. The fiber denier can alternatively be not more than about 12 d, and optionally, can be not more than about 6 d to provide improved effectiveness.

If the fiber denier is too low, the rate of liquid intake into the surge management member may be too slow, and the surge member may not be adequately drained or desorbed by underlying absorbent structure. Additionally, the surge member may not adequately provide the desired temporary-holding and subsequent releasing of the liquid into the retention or storage portion of the absorbent structure. Such factors can lead to premature leakage and excessive skin dampness. If the fiber denier is too large, the surge management member may not adequately decelerate and diffuse surges or gushes of liquid, and may not adequately drain the topsheet layer. For example, there can be poor control of the liquid due to the presence of excessively large capillaries between the large fibers. Additionally, the surge member can be excessively stiff and excessively susceptible to the formation of large, transverse creases. As a result, the article can exhibit poor fit and can be less able to prevent undesired leakage past the laterally opposed sides of the absorbent structure.

In the various configurations of the invention, the selected nonwoven fabric layers of the surge management member 46, such as the first nonwoven fabric layer 52 and/or the second nonwoven fabric layer 56, can have selected properties. In particular aspects, a thickness 58 of the individual nonwoven fabric layer can be at least a minimum of about 0.5 mm, as determined prior to any externally applied compression or lofting. The fabric layer thickness can alternatively be at least about 0.6 mm, and optionally, can be at least about 0.75 mm to provide improved performance. In other aspects, the fabric layer thickness can be not more than a maximum of about 5 mm. The fabric layer thickness can alternatively be not more than about 3.5 mm, and optionally, can be not more than about 1.5 mm to provide improved effectiveness.

If the fabric layer thickness is too low, the surge management member may not adequately decelerate and diffuse the incoming surges or gushes of liquid. Additionally, the surge member may have insufficient void volume to provide the desired temporary-holding of the incoming liquid. If the fabric layer thickness is too large, the surge member can be excessively bulky and provide poor fit.

In another aspect, a selected nonwoven fabric layer (e.g. fibrous layer 52 and/or 56) of the surge management member can have an individual basis weight which is at least a minimum of about 10 g/m$^2$, as determined prior to any externally applied compression or lofting. The basis weight of the individual nonwoven fabric layer can alternatively be at least about 12 g/m$^2$, and optionally, can be at least about 15 g/m$^2$ to provide improved performance. In other aspects, the basis weight of the individual nonwoven fabric layer can be not more than a maximum of about 100 g/m$^2$. The individual basis weight can alternatively be not more than about 65 g/m$^2$, and optionally, can be not more than about 30 g/m$^2$ to provide improved effectiveness.

If the basis weight of the individual nonwoven fabric layer is too low, the surge management member may not adequately decelerate and diffuse the incoming surges or gushes of liquid. Additionally, the surge member may not have sufficient absorptive capacity or void volume to provide the desired temporary holding of incoming liquid. If the basis weight of the individual nonwoven fabric layer is too large, the surge member can be excessively bulky and stiff, and can provide poor fit.

Various elastomeric materials can be employed to form the elastomeric filaments 54. Such elastomeric materials can include thermoplastic elastomeric materials such as diblock, triblock, or multi-block elastomeric copolymers, such as olefinic copolymers, including styrene-isoprene-styrene, styrene-butadiene-styrene, styrene-ethylene/butylene-styrene, or styrene-ethylene/propylene-styrene, which may be obtained from the Shell Chemical Company, under the trade designation KRATON; polyurethanes, including those available from E.I.Du Pont de Nemours Co. under the trade name LYCRA; polyamides, including polyether block amides available from Ato Chemical Company, under the trade name PEBAX; polyesters, such as those available from E.I. Du Pont de Nemours Co., under the trade name HYTREL; and single-site or metallocene-catalyzed polyolefins, including those available from Dow Chemical Co. under the trade name AFFINITY; and the like, as well as combinations thereof. In desired aspects, the elastomeric filaments are composed of an extruded elastomeric material which adheres to at least one of the first nonwoven fabric layer 52 and/or second nonwoven fabric layer 56 of the surge management member. In desired arrangements, the elastomeric filaments 54 are substantially continuous filaments. Optionally, the elastomeric filaments can be discontinuous.

In desired configurations, the elastomeric filaments can be composed of a thermoplastic elastomeric material, such as a styrene-ethylene/butylene-styrene block copolymer material. For example, the elastomeric filaments may be composed of KRATON elastomer material, which is available from Shell Chemical Company a business having offices located in Houston, Tex.

In other aspects, the elastomeric filaments 54 can have a denier which is at least a minimum of about 200 d. The denier of the elastomeric filaments can alternatively be at least about 600 d, and optionally, can be at least about 1300 d to provide desired performance. In other aspects, the elastomeric filaments 54 can have a denier which is not more than a maximum of about 4400 d. The denier of the elastomeric filaments can alternatively be not more than about 3300 d, and optionally, can be not more than about 2200 d to provide improved effectiveness.

If the denier of the elastomeric filaments is too low, the filaments may break too easily and may provide an insufficient force for inducing the desired level of contraction in the surge member 46. As a result, the article can exhibit excessive leakage. If the denier of the elastomeric filaments is too large, the surge member can be excessively contracted, and can provide excessive resistance to the flow of liquid through the z-directional thickness of the surge member.

In further aspects, the elastomeric filaments 54 can have a total basis weight which is at least a minimum of about 5 g/m$^2$. The total basis weight of the elastomeric filaments can alternatively be at least about 15 g/m$^2$, and optionally, can be at least about 30 g/m$^2$ to provide improved performance. In other aspects, the total basis weight of the elastomeric filaments can be not more than a maximum of about 100 g/m$^2$. The total basis weight of the elastomeric filaments can alternatively be not more than about 75 g/m$^2$, and optionally, can be not more than about 50 g/m$^2$ to provide improved effectiveness.

If the total basis weight of the elastomeric filaments is too low, the filaments may provide an insufficient force for inducing the desired level of contraction in the surge member 46. As a result, the article can exhibit excessive leakage. If the total basis weight of the elastomeric filaments is too large, the surge member can be excessively contracted, and there can be an excessive blocking of the flow of liquid through the z-directional thickness of the surge member. In addition, the surge member can be excessively susceptible to the formation of the large creases that can lead to premature leakage.

The elastomeric filaments 54 in the surge management member 46 can be arranged in any operative, regular or irregular, matrix array. In a desired configuration, adjacent elastomeric filaments 54 can be generally parallel to each other. In particular aspects, the elastomeric filaments can have an average spacing which is at least a minimum of about 1 mm. The average spacing can alternatively be at least about 1.5 mm, and optionally, can be at least about 1.7 mm to provide improved performance. In other aspects, the average spacing can be not more than a maximum of about 6 mm. The average spacing can alternatively be not more than about 3 mm, and optionally, can be not more than about 2.3 mm to provide improved effectiveness. In the illustrated configurations, the spacing between adjacent elastomeric filaments 54 extends along the lateral direction 24. Optionally, the spacing between adjacent elastomeric filaments can be along the longitudinal direction 26.

If the average spacing elastomeric filaments is too low, the ability of the surge member 46 to rapidly intake liquid and the ability to move liquid through the z-directional thickness of the surge member can be excessively degraded. Additionally, the surge member may not adequately curve to conform to the shape of the wearer, and can lead to a poor containment of liquid. If the average spacing is too large, the elastomeric filaments may be unable to form the desired contractions in the surge member 46, and may not generate a sufficient void volume in the surge member. Such factors can degrade the ability to reduce leakage past the sides of the containment system.

Desirably, the elastomer filaments 54 and their corresponding elastomeric matrix array have been oriented and joined in an elastomerically stretched state to the selected layer or layers of fabric 52 and 56. For example, a matrix array of the elastomeric filaments 54 can be attached to at least the first nonwoven fabric layer 52 of the surge management member 46 while the elastomeric filaments are in their stretched state. In other examples, the array of elastomeric filaments have been attached to the first and second nonwoven fabric layers 52 and 56 of the surge management member 46 while the elastomeric filaments 54 were in their stretched state. In desired arrangements, the elastomeric filaments 54 have been arranged with their direction of stretch aligned substantially along the longitudinal direction 26 of the article. Alternatively, the elastomeric filaments 54 can be arranged with their direction of stretch substantially aligned along the lateral direction 24.

In desired configurations, the stretched elastomer filaments have been operatively attached between the two facing webs of fibrous surge material 52 and 56. In particular aspects, the elastomer filaments have been stretched to an elongation which is at least a minimum of about 50%. The elongation can alternatively be at least about 200%, and optionally, can be at least about 225% to provide improved performance. In other aspects, the elongation can be not more than a maximum of about 400%. The elongation can alternatively be not more than about 300%, and optionally, can be not more than about 275% to provide improved effectiveness.

If the elongation of the stretched elastomer filaments is too low, the surge member 46 may not have a sufficient z-directional orientation of the fibers in the surge member, and the surge member may be overly susceptible to formation of the large creases that can lead to premature leakage. Additionally, the surge member may not be sufficiently stretchable to allow the desired level of elongation prior to its attachment into the article. If the elongation is too large, the surge management member may be excessively contracted or densified, and may not be able to intake liquid at a sufficiently rapid rate. To help provide the various configurations of the surge member 46, the selected fibrous layer or layers, and the selected elastomer filaments are operatively assembled and joined by a distinctive, low add-on of adhesive. For example, the adhesive can operatively attach the elastomer filaments 54 to at least the first fabric layer 52. Alternatively, the adhesive can be configured to operatively attach the first nonwoven fabric layer 52 to the second nonwoven fabric layer 56. The adhesive can additionally attach the elastomer filaments 54 to either or both of the fabric layers 52 and 56 at a location sandwiched between the fabric layers. In particular aspects, the adhesive has been provided at an add-on basis weight which is at least a minimum of about 0.5 g/m$^2$. The adhesive add-on basis weight can alternatively be at least about 1.5 g/m$^2$, and optionally, can be at least about 2 g/m$^2$ to provide improved performance. In other aspects, the adhesive add-on basis weight can be not more than a maximum of about 50 g/m$^2$. The adhesive add-on basis weight can alternatively be not more than about 30 g/m$^2$, and optionally, can be not more than about 10 g/m² to provide improved effectiveness. In a desired arrangement, the adhesive can be a hot melt adhesive. In other arrangements, the adhesive can be a room temperature, pressure-sensitive adhesive. For example, about 3 g/m² add-on of meltblown, ATO FINDLEY 2525A hot melt adhesive can be applied to assemble the surge material with an advantageous combination of properties.

If the adhesive add-on is to small, the article can exhibit an excessive delamination of the elastic filaments from the nonwoven fabric layers when the fabric layers are stretched from their contracted condition. If the adhesive add-on is too large, the adhesive can excessively restrict the elastomeric properties of the elastic filaments In the various configurations of the invention, the surge management member 46 can have a total, overall thickness which is at least a minimum of about 1 mm. The thickness of the surge member can alternatively be at least about 1.2 mm, and optionally, can be at least about 1.5 mm to provide improved performance. In other aspects, the thickness of the surge member can be not more than a maximum of about 10 mm. The thickness of the surge member can alternatively be not more than about 7 mm, and optionally, can be not more than about 3 mm to provide improved effectiveness. Where the surge management member has been operatively compressed and lofted, such as by the contraction of component elastomeric strands attached and assembled into the surge member, the thickness of overall thickness of the surge management member is determined after the compression and lofting, e.g. after the elastomeric strands have been allowed to contract.

If the thickness of the surge member is too low, the surge management member 46 may not adequately decelerate the flow of incoming liquid, and may have insufficient void volume to provide the desired holding of the incoming liquid. If the thickness of the surge member 46 is too large, the surge member may not be able to transfer liquid to the absorbent body 32 at a sufficiently rapid rate, and the absorbent system may be excessively bulky.

The thickness 58a of the surge management member is determined while the surge member is under a restraining pressure of 1.38 KPa, and while the surge management member is subjected to zero externally-applied tensile forces that would otherwise tend to stretch the surge member.

In other aspects, the fibrous materials (e.g. layers 52 and/or 56) employed to construct the surge management member 46 can have a total, overall basis weight which is at least a minimum of about 20 g/m², when substantially flat-out and ungathered. The basis weight of the surge material can alternatively be at least about 30 g/m², and optionally, can be at least about 60 g/m² to provide improved performance. In other aspects, the basis weight of the surge material can be not more than a maximum of about 300 g/m². The basis weight of the surge material can alternatively be not more than about 200 g/m², and optionally, can be not more than about 100 g/m² to provide improved effectiveness.

Where previously tensioned and stretched elastomer filaments 54 have been incorporated into the surge member 46, a release of the applied tension can allow the elastomer to retract at least partially back towards their unstretched condition. The elastomeric retraction can contract and compress the associated fibrous layer or layers 52 and 56, and the compression can increase the bulk thickness of the individual fabric layers. Additionally, the compression can increase the composite thickness of the overall surge member. The surge management member 46, when in its substantially fully-contracted condition (subjected to a substantially zero level of externally applied tension), can provide a total, composite basis weight of the surge member that is at least a minimum of about 21 g/m². The composite basis weight of the surge member can alternatively be at least about 41 g/m², and optionally, can be at least about 61 g/m² to provide improved performance. In other aspects, the composite basis weight of the surge member can be not more than a maximum of about 390 g/m². The composite basis weight of the surge member can alternatively be not more than about 260 g/m², and optionally, can be not more than about 130 g/m² to provide improved effectiveness.

If the composite basis weight of the surge member is too low, the surge member 46 may have an inadequate absorptive capacity for providing the desired level of temporary holding of the incoming liquid. If the composite basis weight is too large, the surge member 46 may be unable to transfer liquid to the absorbent body 32 at a sufficiently rapid rate, and may be overly stiff and poor fitting.

In particular aspects, one or more of the fabric layers of the surge management member 46, such as the first fabric layer 52 and/or the second nonwoven fabric layer 56, can be configured to have a multiplicity of truncated, mini-pillow regions configured in a selected regular or irregular array, when the surge management layer is observed in its fully contracted state with zero external stress applied thereto. In desired configurations, the mini-pillow regions are configured in an irregular array. The selected array of mini-pillow regions can advantageously provide a multiplicity of tortuous pathways toward either or both of the laterally opposed side edges 98 (e.g. FIG. 5) of the surge management member 46. The array of mini-pillow regions are configured to interrupt a sideways movement of liquid toward the laterally opposed side edges of the surge management member.

In the representatively shown configuration, the elastomeric filaments 54 are selectively configured to compress the bulk material of the nonwoven fabric layer or layers within the surge management member 46 to thereby generate the desired mini-pillow regions.

The mini-pillow regions can have a limited lateral length, and the limited length can advantageously interrupt any pathways that would excessively channel liquid to the side edges of the surge management member. In desired configurations, substantially all of the mini-pillow regions can have a limited lateral length that is a small percentage of the corresponding width dimension 44 of the surge management member at the location of the particular mini-pillow region being assessed. In other aspects, substantially all of the mini-pillow regions can have a lateral length that is not more than about the selected limited length.

In particular aspects of the invention, the surge management member 46 has been attached to the topsheet layer 28 while the surge management member was in a stretched state along its longitudinal direction 26. The attachment of the surge management member 46 to the topsheet layer 28 is configured to operatively hold the surge management member in a stretched state along the longitudinal direction 26 when the topsheet layer 28 is positioned in its substantially flat-out condition. Where the surge management member 46 includes elastomeric components, the attachment of the surge management member 46 to the topsheet layer 28 is configured to hold the surge management member in an elastomerically stretched state along its longitudinal direction 26 when the topsheet layer is positioned in its substantially flat-out condition. For example, where the surge member 46 includes elastomer filaments 54, the elastomeric filaments can be operatively held in an elastomerically stretched state when the topsheet layer is in its substantially flat-out condition. The elongation of the surge management member prior to attachment to the absorbent article can allow the surge member to resist the forming of lateral creases when the concave side of the surge member is subjected to compression as the absorbent article is bent around the contours of the wearer's body.

In other aspects, the surge management member 46 has been elastomerically stretched to an elongation which is at least a minimum of about 2% prior to its attachment to the topsheet layer 28. The elastomeric elongation can alternatively be at least about 3%, and optionally, can be at least about 6% to provide improved performance. In other aspects, the elastomeric elongation of the attached surge member 46 can be not more than a maximum of about 30%. The elastomeric elongation can alternatively be not more than about 15%, and optionally, can be not more than about 12% to provide improved effectiveness.

If the prior elastomeric elongation of the attached surge member is too low, the article may exhibit poor fit, and the surge member may have an inadequate ability to resist the formation of large wrinkles or creases. If the elastomeric elongation is too large, it may be excessively difficult to apply the elongation during the manufacturing of the finished article.

The surge member may also gather excessively, and thereby contribute to excessively leakage.

In still other aspects, the surge management member 46 can be configured to exhibit a maximum tensile force value of not more than about 56 grams-force when the surge management member is elongated or extended 1.95 cm from its fully relaxed state along the longitudinal direction 26. The maximum tensile force value provided by the surge management member 46 can alternatively be not more than about 39 grams-force, and optionally, can be not more than about 18 grams-force when the surge management member is extended 1.95 cm from its fully compressed state to provide improved benefits. A suitable technique for determining the tensile force of the surge management member is set forth in the "Test Procedures" section of the present disclosure.

If the maximum tensile force value of the attached surge member is too low, the surge management member 46 may not have the desired ability to resist the formation of large wrinkles or creases when the surge member is bent. Additionally, the surge member may have insufficient void volume for temporarily holding the incoming liquid. If the maximum tensile force value is too large, the surge member 46 may induce excessively large gathers or creases in other components to which the surge member is joined. Additionally, it may be excessively difficult to generate the desired level of elongation in the surge member during the manufacturing process.

The stretched surge member 46 can exert a low gathering on the component or substrate to which the surge member is primarily attached (e.g. the topsheet layer 28). This low tensile force can discourage the formation of undesirable cross-directional folds or channel creases on the body-side components of the article, such as the topsheet layer 28, the bodyside layer of the wrapsheet 74 or the bodyside portion of the absorbent body 32.

In the various aspects of the invention, the surge management member 46 can include a length-wise compressible material that is attached to the selected absorbent article in either a selected, tensioned or elongated state; or in a completely retracted or otherwise untensioned state. When the article and surge member 46 are subsequently bowed or otherwise bent into a curved shape, such as occurs when an absorbent product is applied to and wrapped around a wearer, the surge member can substantially avoid the formation of undesired channel creases that are generally aligned transversely along the article cross-direction 24, and extend over a significant portion of the width 44 of the surge member that corresponds to the location of the channel crease. The bending compression that occurs along the concave surface portion of the surge member can be readily accommodated by the surge member without the gross buckling and collapsing of the surge material that contributes to the formation of continuous troughs or grooves that extend to the terminal side edges 98 of the surge member 46.

Where the surge member has been pre-stretched prior to its assembly into the final article 10, the bending compression that is induced along the concave surface portion of the surge member can effectively relax the residual tension along the concave surface portion and allow the inside-facing, concave surface to retract towards to its fully retracted state. Additionally, where the surge member 46 has a desired low density, the fibers of the surge material can operatively "pack" on the concave surface of the surge member without reaching an overly high density that would excessively inhibit the desired intake rate of the absorbed liquid.

The leg elastic members 34 are located in the lateral side margins 20 of diaper 10, and are arranged to draw and hold diaper 10 against the legs of the wearer. The elastic members are secured to diaper 10 in an elastically contractible condition so that in a normal under strain configuration, the elastic members effectively contract against diaper 10. The elastic members can be secured in an elastically contractible condition in at least two ways; for example, the elastic members may be stretched and secured while diaper 10 is in an uncontracted condition. Alternatively, diaper 10 may be contracted, for example, by pleating, and the elastic members secured and connected to diaper 10 while the elastic members are in their relaxed or unstretched condition. Still other mechanisms, such as heat-shrink elastic material, may be used to gather the garment.

In the embodiment illustrated in FIGS. 1 and 2, the leg elastic members 34 extend essentially along the complete length of the intermediate crotch region 16 of diaper 10. Alternatively, elastic members 34 may extend the entire length of diaper 10, or any other length suitable for providing the arrangement of elastically contractible lines desired for the particular diaper design.

The elastic members 34 may have any of a multitude of configurations. For example, the width of the individual elastic members 34 may be varied from about 0.25 millimeters (about 0.01 inch) to about 25 millimeters (about 1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded; heat and pressure sealed using a variety of bonding patterns, or adhesively bonded to diaper 10 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands may be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 10 can include a waist elastic 42 positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (FIG. 1).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along a ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, an elastomeric neck-bonded-laminate (NBL) material, an elastomeric film, an elastomeric foam material, or the like, which is elastomerically stretchable at least along the lateral direction 24. For example, suitable meltblown elastomeric fibrous webs for forming ear regions 38 are described in U.S. Pat. No. 4,663,220 by T. Wisneski et al. which issued May 5, 1987, the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 by Mormon which issued Jul. 13, 1993, the entire disclosure of which is hereby incorporated by reference in a manner that is consistent herewith.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 by P. VanGompel et al. which issued Jul. 3, 1990, the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30. Additionally, a second pair of ear regions may be included to extend laterally at the opposed lateral ends of the front waistband section of the backsheet. The illustrated ear regions have a tapered, curved or otherwise contoured shape in which the longitudinal length of the relatively inboard base region is larger or smaller than the longitudinal length of its relatively outboard end region. Alternatively, the ear regions may have a substantially rectangular shape, and optionally may have a substantially trapezoidal shape.

Diaper 10 can also include a pair of elasticized containment flaps 62 with elastic members 68 (e.g. FIG. 1) which extend generally length-wise along the longitudinal direction 26 of the diaper. The containment flaps are typically positioned laterally inboard from leg elastics 34, and substantially symmetrically placed on each side of the lengthwise, longitudinal centerline of the diaper. In the illustrated arrangements, each containment flap 62 has a substantially fixed edge portion 64 and a substantially moveable edge portion 66, and is operably elasticized to help each containment flap to closely contact and conform to the contours of the wearer's body. Examples of suitable containment flap constructions are described in U.S. Pat. No. 4,704,116 by K. Enloe which issued Nov. 3, 1987, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. Pat. 5,562,650 entitled ABSORBENT ARTICLE HAVING AN IMPROVED SURGE MANAGEMENT by R. Everett et al., which issued Feb. 13, 1996, the disclosure of which is hereby incorporated by reference in a manner that is consistent herewith.

Still other configurations of the invention can include a combination component that provides an elasticized leg gusset and a corresponding containment flap along each side edge region of the absorbent article. Examples of such articles are described in U.S. Pat. No. 5,904,675 entitled AN ABSORBENT ARTICLE WITH IMPROVED ELASTIC MARGINS AND CONTAINMENT SYSTEM by D. Laux et al., which issued May 18, 1999; and U.S. Pat. No. 5,993,433 entitled ABSORBENT ARTICLE WITH ENHANCED ELASTIC DESIGN FOR IMPROVED AESTHETICS AND CONTAINMENT by R. G. St. Louis et al., which issued Nov. 30, 1999. The entire disclosures of these documents are hereby incorporated by reference in a manner that is consistent herewith.

In optional configurations of the invention, diaper 10 may include internal, elasticized, containment waist flaps, such as those described in U.S. Pat. No. 4,753,646 issued Jun. 28, 1988, to K. Enloe; and in U.S. Pat. No. 5,827,259 entitled AN ABSORBENT ARTICLE WITH IMPROVED WAIST ELASTIC AND CONTAINMENT SYSTEM by D. Laux et al., which issued Oct. 27, 1998; the entire disclosures of which are hereby incorporated by reference in a manner that is consistent herewith. Similar to the construction of the containment flaps, the containment waist flaps may be composed of a wettable or non-wettable material, as desired. The waist flap material may be substantially liquid-impermeable, permeable to only gas, or permeable to both gas and liquid.

To provide a desired refastenable fastening system, diaper 10 can include one or more, appointed landing member regions or patches, such as provided by the representatively shown, primary landing member 50. The landing member can provide an operable target area for generating a releasable and re-attachable securement with at least one of the fastener tabs 36. In desired embodiments of the invention, the landing member patch can be positioned on the front waistband portion 14 of the diaper and located on the outward surface of the backsheet layer 30. Alternatively, the landing member patch can be positioned on an appointed inward surface of the diaper, such as the bodyside surface of the topsheet layer 28.

Particular arrangements of the invention can include one or more landing members 50 which can be directly or indirectly attached to the second waistband portion 14. Desirably, the landing members are affixed directly to the outward surface of the appropriate waistband portion, but may optionally be joined to the inward, bodyside surface of the article waistband portion.

In the various configurations of the invention, the landing member 50 can be composed of a substantially non-elastomeric material, such as polymer films or tapes, woven fabrics, nonwoven fabrics or the like, as well as combinations thereof. In particular configurations of the invention, the landing member may be composed of a substantially elastomeric material, such as a stretch-bonded-laminate (SBL) material, an elastomeric neck-bonded-laminate (NBL) material, an elastomeric film, an elastomeric foam material, or the like, which is elastomerically stretchable at least along the lateral direction 24.

The various configurations of the invention can include at least one separately provided fastener tab 36 located at either or both of the lateral end regions 86 of the back waistband 12. Alternatively, the at least one separately provided fastener tab 36 can be located at either or both of the lateral end regions 88 of the front waistband 14. The representatively shown embodiment, for example, has a laterally opposed pair of the fastener tabs 36 with a one of the fastener tabs located at each of the distal side edges of the rear waistband 12. More particularly, each of the fasteners 36 is assembled and attached to project and extend from a corresponding, immediately adjacent ear region located at one of the opposed, lateral end regions 86 of the front waistband section 12.

The fastener tab 36 can have any operative shape. For example, the shape of the fastener tab may be rectangular, trapezoidal, sinusoidal, rectilinear, curvilinear or the like, as well as combinations thereof. The laterally outboard, terminal edge of the fastener tab may be rectilinear or curvilinear, and as representatively shown, the terminal edge may be contoured to provide a protruding finger tab region.

The fastener tab 36 can be composed of a substantially non-elastomeric material, such as polymer films or tapes, woven fabrics, nonwoven fabrics or the like, as well as combinations thereof. Optionally, the fastener tab may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24.

In the various aspects and configurations of the invention, the fastening mechanism between the selected first fastener component and the selected, second fastener component may be adhesive, cohesive, mechanical or combinations thereof. In the context of the present invention, a mechanical fastening system is a system which includes cooperating, first and second components which mechanically interengage to provide a desired securement.

Desirably, the first and second fastener components include complementary elements of a cooperatively interengaging mechanical fastening system. The mechanical fastener components can be provided by mechanical-type fasteners such as hooks, buckles, snaps, buttons and the like, which include cooperating and complementary, mechanically interlocking components.

As shown in the illustrated arrangements, for example, the mechanical fastening system may be a hook-and-loop type of fastening system. Such fastening systems typically include attachment members having the form of a "hook" or hook-like, male component, and include a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single-prong hook configuration, a multiple-prong hook configuration or by a generally continuous, expanded-head configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

A configuration which employs a selectively releasable, interengaging mechanical fastening system can, for example, locate the first fastener component on at least the appointed mating or securing surface of the fastener tab 36, and can locate the cooperating, second fastener component on the appointed engagement surface of the appointed landing member 50. For example, with the representatively shown hook-and-loop fastener, the fastening component which is attached to the appointed mating or securing surface of the fastener tab 36 may include a hook type of mechanical engagement element, and the complementary fastening component, which is operably joined and attached to the appointed landing zone member 50 can include a loop type of fastening element.

It should also be readily apparent that, in the various configurations of the invention, the relative positions and/or materials of the first fastening component and its cooperating, complementary second fastening component can be transposed. Accordingly, the fastening component, which is attached to the appointed mating surface of the fastener tabs 36, may include the loop type of mechanical fastening element; and the complementary, second fastening component, which is operatively joined and attached to the appointed landing zone member, can include the hook type of attachment members.

Examples of hook-and-loop fastening systems and components are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in to U.S. Pat. No. 5,605,735 entitled HIGH-PEEL TAB FASTENER by G. Zehner et al., which was filed Dec. 28, 1994; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith. Examples of fastening tabs constructed with a carrier layer are described in U.S. Pat. No. 5,624,429 entitled MECHANICAL FASTENING SYSTEM WITH GRIP TAB by A. Long et al., which issued Apr. 29, 1997, the entire disclosure of which is hereby incorporated by reference in a manner which is consistent herewith.

For the various configurations of the invention, an example of a suitable attachment hook member is a micro-hook member provided in a material which is distributed under the designation VELCRO HTH 829, and is available from VELCRO U.S.A., Inc., a business having offices in Manchester, New Hampshire. The micro-hook material has attachment members in the shape of angled, prong-type hook members. The hook members can be configured with a hook height which is within the range of about 0.030–0.063 cm (about 0.012–0.025 inch); and a hook width which is within the range of about 0.007 to 0.022 cm (about 0.003 to 0.009 inch). The hook elements are molded onto a base layer substrate having a thickness of about 0.0076–0.008 cm (about 0.003–0.0035 inch), and the hook material has a Gurley stiffness of about 12 mgf (about 12 Gurley units). Other suitable hook members can be found on VELCRO HTH 858, VELCRO HTH 851 and VELCRO HTH 863 hook materials. Another suitable type of attachment hook member can be found on a 3M CS200 material available from the 3M Company, a business having offices in St. Paul, Minnesota.

For the purposes of the present disclosure, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various configurations of the invention, the loop material can be provided by a nonwoven, woven or knit fabric, as well as combinations thereof. For example, a suitable loop material fabric can be composed of a 2 bar, warp knit fabric of the type available from Guilford Mills, Inc., Greensboro, N.C. under the trade designation #34285, as well as other types of knit fabrics. Suitable loop materials are also available from the 3M Company, which has distributed a nylon woven loop under their SCOTCHMATE brand. The 3M Company has also distributed a liner-less loop web with adhesive on the backside of the web, and 3M knitted loop tape.

The loop material may also include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web nonfibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled PATTERN-UNBONDED NONWOVEN WEB AND PROCESS FOR MAKING THE SAME, by T. J. Stokes et al., which issued Jan. 12, 1999; the entire disclosure of which is incorporated herein by reference in a manner that is consistent herewith.

The loop material employed in the various configurations of the invention need not be limited to a discrete or isolated patch on the outward surface of the article. Instead, the loop material can be provided by a substantially continuous, outer fibrous layer which is assembled, integrated or otherwise joined to extend over a predetermined surface area of the desired article. For example, the outer fibrous layer may be arranged to extend over substantially the total exposed surface area of a cloth-like outer cover employed with the article.

In the various configurations of the invention, the engagement force between the selected first fastener component and its appointed and cooperating second fastener component should be large enough and durable enough to provide an adequate securement of the article on the wearer during use.

TEST PROCEDURES

Retractive Tensile Force

A suitable technique for determining the tensile force provided by the surge management member is the following procedure:

Remove the surge management test specimen from individual product article, each test specimen is desirably removed from the product article at a location which is centered along both the longitudinal dimension and lateral dimension of the surge management portion of the product article. Each specimen is inserted into the jaws of the test apparatus making sure not to stretch the specimen. Each specimen is pulled until a 95 percent drop from the peak load is reached. Tensile force measurements are taken at specified test strain points, particularly at an elongation 1.95 cm. The test strain points are calculated or otherwise determined from the initial test gage length of a specimen. Other test specifications include:

Testing hardware: MTS 1/G Tensile Tester

Testing Software: TESTWORKS for WINDOWS Version 3.10

Specimen Width is 2.5 inch (6.35 cm)

Load Cell: 10 lb (4.54 kg)

Test Speed: 500 mm/min.

Gage Length: 130 mm

The following examples are given to provide a more detailed understanding of the invention. The particular materials, dimensions, amounts and other parameters are exemplary, and are not intended to specifically limit the scope of the invention.

EXAMPLE 1

The conventional surge management member of Example 1 was a through-air bonded carded web, which was composed of 40 percent, 6 denier polyester filaments and 60 percent, 3 denier bicomponent filaments. The surge management member had a finished basis weight of 3.55 ounces per square yard (120 g/m$^2$) and a density of 0.024 g/cm$^3$. The web was substantially monolithic in that it was not a laminate. Additionally, the web had a machine-direction (MD) and a cross-direction (CD).

For the purposes of the present disclosure, the machine-direction (MD) of a material is the dimension of the material which is substantially parallel to the direction along which the material was transported through its manufacturing process. Additionally, a cross-direction (CD) of the material is perpendicular to the machine-direction, and lies substantially parallel to the x-y plane of the manufactured material.

The surge material had a relatively high density and a relatively high fiber orientation and alignment along its lengthwise machine-direction. As a result, the surge material provided a relatively high beam stiffness. When the MD of the surge material was bent around the curvature that represented the contours of a wearer's body, the material buckled and produced large and deep creases or folds that extended generally parallel to the axis about which the material was bent.

EXAMPLE 2

The surge management material of Example 2 was composed of two webs or plies of a nonwoven fabric which had the following composition and structure: about 40% polyester staple fiber of approximately 6 denier; about 60% bicomponent binder fiber of an approximate nominal 3 denier. Each web had an ungathered basis weight of approximately 17 grams per square meter (g/m$^2$) to provide a total, nonwoven fabric basis weight of about 34 g/m$^2$.

A 2 g/m$^2$ add-on of meltblown, ATO FINDLEY 2525A hot melt adhesive was applied to an appointed inside surface of one of the 17 g/m$^2$ webs of the surge material. The adhesive is available from Ato Findley, Inc., a business having offices located in Wauwatosa, Wis.

An elastomer matrix was provided at a basis weight of approximately 15 g/m$^2$, and was composed of filamentary SHELL G2740 KRATON elastomer. The elastomeric matrix was stretched in a lengthwise machine-direction of the matrix, and was applied in its stretched state between the two webs surge management material.

The completed, composite laminate was allowed to retract under a condition of zero applied external stress, and the retracted composite had a total, gathered basis weight of 115 g/m$^2$. The surge management material, in its retracted form, included 85 g/m$^2$ total of the staple fiber/bicomponent binder fiber nonwoven fabric; 15 g/m$^2$ total of the KRATON elastomer filaments; and approximately 15 g/m$^2$ total of the meltblown ATO FINDLEY 2525A adhesive.

A suitable method and apparatus for producing the surge management material can include a Vertical Filament Lamination (VFL) process, which is described in U.S. patent application Ser. No. 09/855,169 entitled METHOD AND APPARATUS FOR PRODUCING LAMINATED ARTICLES by H. M. Welch et al. which was filed May 14, 2001. Additional description is provided in U.S. patent application Ser. No. 09/855,144 entitled ELASTIC STRANDED LAMINATE WITH ADHESIVE BONDS AND METHOD OF MANUFACTURE by H. M. Welch et al. which was filed May 14, 2001. The entire disclosures of these documents are incorporated herein by reference in a manner that is consistent herewith.

The resultant surge management member constructed with the surge material of this Example 2 provided a lofty and easily bendable structure that did not produce large creases or folds that extended along the cross-direction when the surge member was bent around a curvature that represented the contours of a wearer's body.

COMPARATIVE TESTING

A "prone" cradle, saline runoff test was conducted to compare the runoff resistance of surge management members constructed from the materials described for Examples 1 and 2. The "prone" cradle was shaped like a U lying on its side, simulating an infant sleeping on its belly.

The nonwoven surge material of Example 1 was cut to provide a sample which measured 6 inches (15.24 cm) in its machine-direction length, 2.5 inches (6.35 cm) in its cross-direction width. The MD of the surge material was aligned along the longitudinal direction 26 of a conventional absorbent pad composed of woodpulp fluff and superabsorbent particles, and the surge material was attached to the absorbent pad employing double-sided adhesive tape placed along the lengthwise edges of the surge material to provide another test assembly.

The nonwoven laminate surge material of Example 2 was cut to provide a sample which measured 5.5 inches (13.97 cm) along its machine-direction (MD) length and 2.5 inches (6.35 cm) along its cross-direction (CD) width. The surge material was stretched to a length of 6 inches (15.24 cm) along its MD length, and the MD of the surge material was aligned along the longitudinal direction 26 of a conventional absorbent pad composed of woodpulp fluff and superabsorbent particles. While the surge material was held in its stretched condition, the surge material was attached to the absorbent pad employing double-sided adhesive tape placed along the lengthwise edges of the surge material to provide a test assembly.

Each absorbent-surge test assembly was placed into a bench test cradle and set into the prone position, with the plastic, U-shaped cradle lying on its side to simulate an infant sleeping on its belly. Three quantities ("insults") of saline solution were dispensed into the selected test assembly, and each individual quantity had a volume of 80 ml. The liquid saline was dispensed at a rate of 15 ml/sec with 30-minute intervals between the dispensing of the individual quantities. The saline solution was applied to the selected test assembly at a location that was 5 inches (12.7 cm) away from the edge of the absorbent that was appointed for placement proximate the front waistband portion of the final article. Any resulting runoff of the saline solution was collected and weighed, and the results are set forth in the following Table 1:

TABLE 1

|  | Example 1 | Example 2 |
| --- | --- | --- |
| First Insult Runoff | 6.1 gm | 4.2 gm |
| Second Insult Runoff | 17.8 gm | 8.1 gm |
| Third Insult Runoff | 40 gm | 19.2 gm |

It can be seen that the conventional surge management member constructed in accordance with Example 1 produced more runoff as compared to the distinctive surge management member constructed in accordance with Example 2.

Gurley Stiffness testing were conducted on surge management members that were composed of the surge management materials described in Examples 1 and 2. The testing results are summarized in the following Table 2.

TABLE 2

|  | Example 1 MD (N = 5) | Example 2 MD (N = 5) | Example 1 CD (N = 5) | Example 2 CD (N = 5) |
| --- | --- | --- | --- | --- |
| Gurley Stiffness Avg. (mgf) | 36.3 | 9.7 | 13.4 | 24.5 |
| Gurley Stiffness Range (mgf) | 27.5–52.1 | 9.1–10.1 | 10.1–15.1 | 20.5–29.5 |

The Gurley Stiffness measurement can be conducted in accordance with TAPPI Standard STP 560. The Gurley stiffness values are given in the traditional units of "milligrams-force" (mgf), which are equivalent to the currently employed "Gurley Units". "Gurley Stiffness MD" tested the samples of surge material with the sample being bent and curved along its MD dimension. The approximately four-fold higher value for the material of Example 1 indicates its higher stiffness, which contributes to its higher tendency to buckle and produce unwanted creases and folds.

"Gurley Stiffness CD" tested the samples of surge material with the sample being bent and curved along its CD dimension. The "Gurley Stiffness CD" results show that the samples of the surge material of Example 2 were approximately two times stiffer in their as-produced cross-direction, as compared to the samples of the surge material of Example 1.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An absorbent article having longitudinal direction and a lateral direction, said article comprising:
   a backsheet layer;
   a liquid-permeable topsheet layer;
   an absorbent body sandwiched between said backsheet layer and said topsheet layer; and
   a surge management member interposed between said topsheet layer and said absorbent body;
   said surge management member having a thickness dimension and including a first nonwoven fabric layer; at least a second nonwoven fabric layer joined with said first nonwoven fabric layer; and a plurality of elastomeric filaments sandwiched between said first and second nonwoven fabric layers, said elastomeric filaments being generally parallel to each other and either extending along a lateral or longitudinal direction only are to at least one of said first and second nonwoven fabric layers of the surge management member to provide primarily in one direction only of longitudinally compression said surge management member and to loft said thickness of said surge management member.

2. An absorbent article as recited in claim 1, wherein said elastomeric filaments are attached to at least one of said first and second nonwoven fabric layers of the surge management member to longitudinally compress said first and second fabric layers, and to loft an overall total thickness of said first and second fabric layers.

3. An absorbent article as recited in claim 1, further including an adhesive which operatively attaches said first nonwoven fabric layer to said second nonwoven fabric layer, said adhesive having been provided at an add-on basis weight of not more than about 50 g/m².

4. An absorbent article as recited in claim 1, wherein said elastomeric filaments are configured to longitudinally compress and loft said first and second nonwoven fabric layers of the surge management member.

5. An absorbent article as recited in claim 2, wherein said surge management member, when in its substantially fully-compressed condition, includes:
   a total basis weight of nonwoven fabric that is at least about 21 g/m²;
   a total basis weight of elastomeric filaments that is at least about 5 g/m²; and
   a total basis weight of adhesive that is not more than about 50 g/m².

6. An absorbent article as recited in claim 1, wherein said surge management member has been attached to said topsheet layer while said surge management member was stretched along its longitudinal direction.

7. An absorbent article as recited in claim 6, wherein said attachment of said surge management member to said topsheet layer is configured to operatively hold said surge management member in an elastomerically stretched state along said longitudinal direction when said topsheet layer is positioned in its substantially flat-out condition.

8. An absorbent article as recited in claim 1, wherein said elastomeric filaments have been attached to said first nonwoven fabric layer of the surge management member while said elastomeric filaments were in a stretched state along said longitudinal direction.

9. An absorbent article as recited in claim 8, wherein said elastomeric filaments have been elastomerically stretched at least about 200% prior to their attachment to said first nonwoven fabric layer.

10. An absorbent article as recited in claim 1, wherein said surge management member has been elastomerically stretched at least about 2% prior to its attachment to said topsheet layer.

11. An absorbent article as recited in claim 1, wherein said elastomeric filaments are substantially continuous filaments.

12. An absorbent article as recited in claim 1, wherein said elastomeric filaments have a denier of not more than about 4400 d.

13. An absorbent article as recited in claim 1, wherein said elastomeric filaments have a denier of not less than about 200 d.

14. An absorbent article as recited in claim 1, wherein said elastomeric filaments have an average spacing of not more about 6 mm between adjacent filaments.

15. An absorbent article as recited in claim 1, wherein said elastomeric filaments have a spacing of at least about 1 mm.

16. An absorbent article as recited in claim 1, wherein said elastomeric filaments are composed of an elastomeric material which adheres to at least said first nonwoven fabric layer of the surge management member.

17. An absorbent article as recited in claim 1, wherein said elastomeric filaments are composed of an elastomeric, multi-block, olefinic copolymer material.

18. An absorbent article as recited in claim 1, wherein at least one of said first and second nonwoven fabric layers of the surge management member includes a bonded-carded web composed of polyester fibers and bicomponent fibers.

19. An absorbent article as recited in claim 1, wherein at least one of said first and second nonwoven fabric layers of said surge management member includes a fabric composed of about 40% polyester fibers of approximately 6 denier; and about 60% of bicomponent of approximately 3 denier.

20. An absorbent article as recited in claim 1, wherein said surge management member has a composite thickness of at least about 1 mm, as determined under a restraining pressure of 1.38 KPa.

21. An absorbent article as recited in claim 1, wherein said first nonwoven layer of said surge management member includes
   a thickness of at least about 0.5 mm; and
   a basis weight of at least about 10 g/m².

22. An absorbent article as recited in claim 1, wherein said second nonwoven layer of the surge management member includes a thickness of at least about 0.5 mm; and a basis weight of at least about 10 g/m².

23. An absorbent article as recited in claim 1, wherein
   said first nonwoven fabric layer of the surge management member provides a multiplicity of truncated, mini-pillow regions configured in an irregular array, when the surge management member is observed in its fully contracted state with zero external stress applied thereto; and
   said array of mini-pillow regions provides a multiplicity of tortuous pathways toward laterally opposed side edges of said surge management member.

24. An absorbent article as recited in claim 23, wherein said array of mini-pillow regions are configured to interrupt a sideways movement of liquid toward laterally opposed side edges of said surge management member.

25. An absorbent article as recited in claim 24, wherein substantially none of said mini-pillow regions has a lateral length that extends across an entire, corresponding lateral width of said surge management member.

* * * * *